United States Patent [19]
Harcourt

[11] Patent Number: 6,010,452
[45] Date of Patent: Jan. 4, 2000

[54] ARTICLE, SYSTEM AND METHOD FOR DETERMINING A FITNESS AGE FOR AN INDIVIDUAL

[75] Inventor: Kristian L. Harcourt, Sydney, Australia

[73] Assignee: Fitnessage, Inc., La Jolla, Calif.

[21] Appl. No.: 09/138,834

[22] Filed: Aug. 24, 1998

[51] Int. Cl.$^7$ ...................................................... A61B 5/00
[52] U.S. Cl. .............................................................. 600/300
[58] Field of Search ..................... 600/300; 482/900–902

[56] References Cited

U.S. PATENT DOCUMENTS

| | | | |
|---|---|---|---|
| 4,367,752 | 1/1983 | Jimenez et al. | 128/689 |
| 5,435,315 | 7/1995 | McPhee et al. | 128/670 |
| 5,931,763 | 8/1999 | Alessandri | 482/4 |

Primary Examiner—Max Hindenburg
Attorney, Agent, or Firm—Philip J. Anderson; Quirk & Tratos

[57] ABSTRACT

An article, system and method for calculating an individual's overall fitness age using one or more measurable fitness parameters. Among the parameters used are heart recovery rate, flexibility, strength and body fat composition. A data processor contains data structures that correlate heart recovery rate to a heart recovery fitness age, flexibility to a flexibility fitness age, strength to a strength fitness age and body fat composition to a body composition fitness age. When the physically measured parameters are input into the processor, the processor determines the fitness age corresponding to each measurement and calculates the overall fitness age using the formula:

Overall Fitness Age=(0.30) heart recovery fitness age+(0.21) flexibility fitness age+(0.21) strength fitness age+(0.28) body composition fitness age.

The overall fitness age is then displayed.

7 Claims, 10 Drawing Sheets

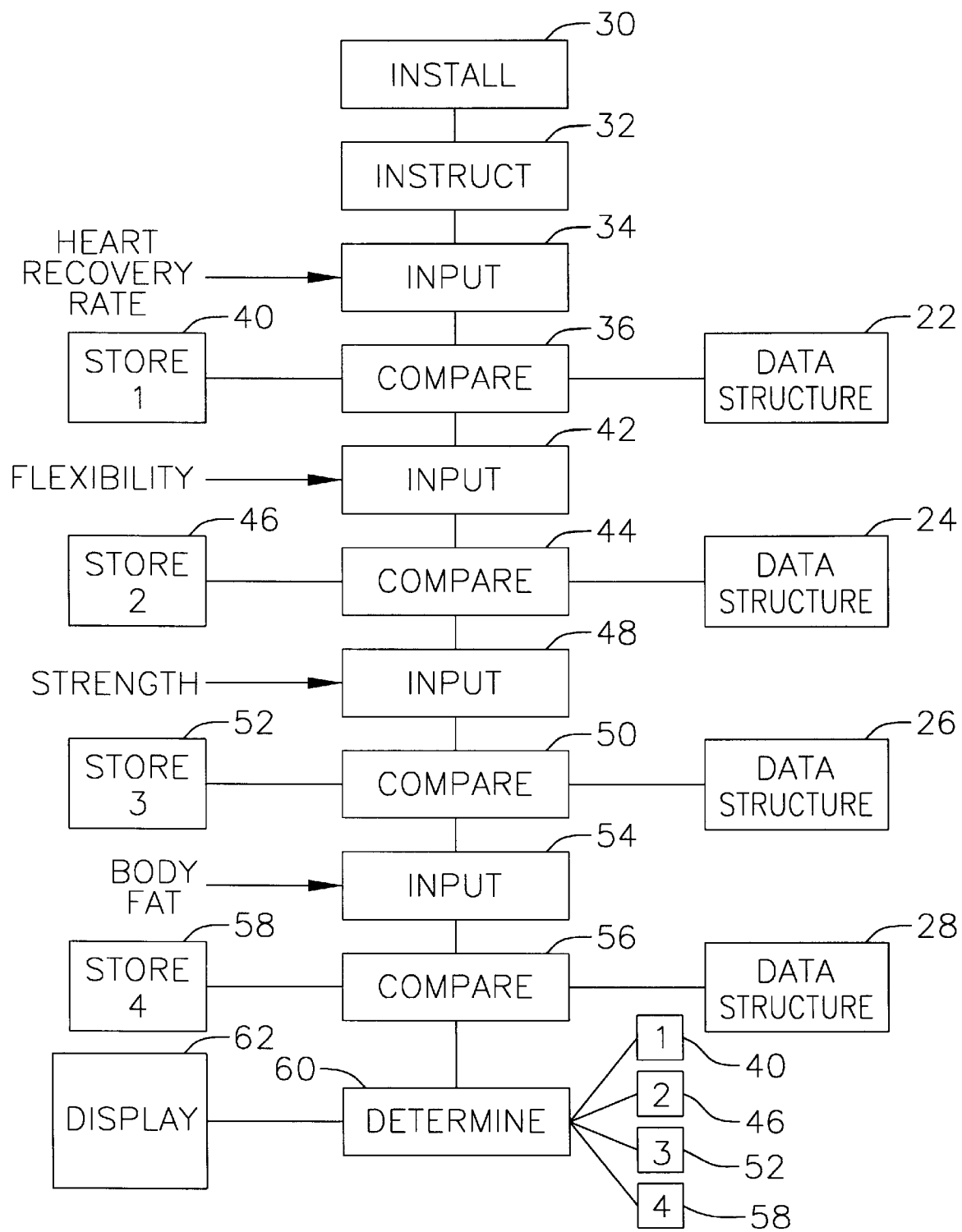

FIG.3A

| RECOVERY RATE(MEN) | FITNESS AGE | RECOVERY RATE(WOMEN) | FITNESS AGE |
|---|---|---|---|
| 80 | 18 | 86 | 18 |
| 81 | 19 | 87 | 18 |
| 82 | 19 | 88 | 19 |
| 83 | 19 | 89 | 19 |
| 84 | 19 | 90 | 19 |
| 85 | 19 | 91 | 19 |
| 86 | 20 | 92 | 19 |
| 87 | 20 | 93 | 20 |
| 88 | 20 | 94 | 20 |
| 89 | 20 | 95 | 20 |
| 90 | 20 | 96 | 20 |
| 91 | 20 | 97 | 20 |
| 92 | 20 | 98 | 20 |
| 93 | 21 | 99 | 21 |
| 94 | 21 | 100 | 21 |
| 95 | 21 | 101 | 21 |
| 96 | 21 | 102 | 21 |
| 97 | 21 | 103 | 21 |
| 99 | 22 | 104 | 21 |
| 97 | 22 | 105 | 22 |
| 98 | 22 | 106 | 22 |
| 99 | 23 | 107 | 22 |
| 100 | 23 | 108 | 22 |
| 101 | 23 | 109 | 22 |
| 102 | 23 | 110 | 23 |
| 103 | 30 | 111 | 23 |
| 104 | 32 | 112 | 23 |
| 105 | 34 | 113 | 27 |
| 106 | 36 | 114 | 30 |
| 107 | 38 | 115 | 35 |
| 108 | 40 | 116 | 40 |
| 109 | 45 | 117 | 45 |
| 110 | 50 | 118 | 50 |
| 111 | 55 | 119 | 55 |
| 112 | 60 | 120 | 60 |
| 113 | 65 | 121 | 64 |
| 114 | 72 | 122 | 68 |
| 115 | 73 | 123 | 72 |
| 116 | 74 | 124 | 73 |
| 117 | 75 | 125 | 74 |
| 118 | 76 | 126 | 75 |
| 119 | 77 | 127 | 76 |
| 120 | 78 | 128 | 77 |
| 121 | 79 | 129 | 78 |
| 122 | 80 | 130 | 79 |
| 123 | 80 | 131 | 80 |

FIG.4A

NUMBERS REPRESENT INCHES REACHED WITH TOES AS THE REFERENCE POINT.

| AGE GROUP | 18-29 | | 30-39 | | 40-49 | | 50-59 | | 60- | |
|---|---|---|---|---|---|---|---|---|---|---|
| | MEN | WOMEN | MEN | WOMEN | MEN | WOMEN | MEN | WOMEN | MEN | WOMEN |
| EXCELLENT | 6 | 8 | 5 | 7 | 4 | 6 | 3 | 5 | 2 | 4 |
| GOOD | 3 | 6 | 2 | 5 | 1 | 4 | 0 | 3 | -1 | 2 |
| AVERAGE | -3 | 0 | -4 | -1 | -5 | -2 | -6 | -3 | -7 | -4 |
| FAIR | -6 | -3 | -7 | -4 | -8 | -5 | -9 | -6 | -10 | -7 |
| POOR | <-6 | <-3 | <-7 | <-4 | <-8 | <-5 | <-9 | <-6 | <-10 | <-7 |

FIG.4B

| MEN | FITNESS AGE | WOMEN | FITNESS AGE |
|---|---|---|---|
| 6 | 18 | 6 | 18 |
| 5 | 19 | 5 | 20 |
| 4 | 19 | 4 | 25 |
| 3 | 20 | 3 | 35 |
| 2 | 22 | 2 | 45 |
| 1 | 25 | 1 | 55 |
| 0 | 35 | 0 | 65 |
| -1 | 45 | 1 | 70 |
| -2 | 55 | 2 | 72 |
| -3 | 65 | 3 | 75 |
| -4 | 75 | 4 | 80 |
| -5 | 80 | 5 | 80 |
| -6 | 80 | 6 | 80 |

FIG. 5A

NUMBERS REPRESENT NUMBER OF PUSH UPS.

| AGE GROUP | 18-29 | | 30-39 | | 40-49 | | 50-59 | | 60-80 | |
|---|---|---|---|---|---|---|---|---|---|---|
| | MEN | WOMEN | MEN | WOMEN | MEN | WOMEN | MEN | WOMEN | MEN | WOMEN |
| EXCELLENT | 54 | 48 | 44 | 39 | 39 | 34 | 34 | 29 | 29 | 19 |
| GOOD | 44 | 33 | 35 | 24 | 29 | 19 | 24 | 14 | 19 | 4 |
| AVERAGE | 34 | 16 | 24 | 11 | 19 | 7 | 14 | 5 | 9 | 2 |
| FAIR | 19 | 5 | 14 | 3 | 11 | 2 | 7 | 1 | 4 | 0 |
| POOR | <19 | <5 | <14 | <3 | <11 | <2 | <7 | <1 | <4 | 0 |

FIG. 6A

NUMBERS REPRESENT NUMBER OF SIT UPS.

| AGE GROUP | 18-29 | | 30-39 | | 40-49 | | 50-59 | | 60-80 | |
|---|---|---|---|---|---|---|---|---|---|---|
| | MEN | WOMEN | MEN | WOMEN | MEN | WOMEN | MEN | WOMEN | MEN | WOMEN |
| EXCELLENT | 47 | 43 | 39 | 35 | 34 | 30 | 29 | 25 | 24 | 20 |
| GOOD | 42 | 38 | 34 | 30 | 29 | 25 | 24 | 20 | 19 | 15 |
| AVERAGE | 36 | 32 | 28 | 24 | 23 | 18 | 18 | 14 | 13 | 9 |
| FAIR | 32 | 28 | 24 | 20 | 19 | 15 | 14 | 10 | 9 | 5 |
| POOR | <32 | <28 | <24 | <20 | <19 | <15 | <14 | <10 | <9 | <5 |

FIG.5B

| MEN | FITNESS AGE | WOMEN | FITNESS AGE |
|---|---|---|---|
| 45 | 18 | 34 | 18 |
| 44 | 20 | 33 | 19 |
| 43 | 21 | 32 | 20 |
| 42 | 22 | 31 | 20 |
| 41 | 23 | 30 | 21 |
| 40 | 24 | 29 | 22 |
| 39 | 25 | 28 | 23 |
| 38 | 26 | 27 | 24 |
| 37 | 27 | 26 | 25 |
| 36 | 28 | 25 | 25 |
| 35 | 29 | 24 | 26 |
| 34 | 31 | 23 | 28 |
| 33 | 32 | 22 | 29 |
| 32 | 33 | 21 | 30 |
| 31 | 34 | 20 | 31 |
| 30 | 35 | 19 | 33 |
| 29 | 37 | 18 | 35 |
| 28 | 39 | 17 | 37 |
| 27 | 41 | 16 | 39 |
| 26 | 43 | 15 | 41 |
| 25 | 45 | 14 | 43 |
| 24 | 47 | 13 | 45 |
| 23 | 49 | 12 | 48 |
| 22 | 51 | 11 | 52 |
| 21 | 53 | 10 | 55 |
| 20 | 55 | 9 | 57 |
| 19 | 57 | 8 | 58 |
| 18 | 59 | 7 | 60 |
| 17 | 61 | 6 | 61 |
| 16 | 63 | 5 | 63 |
| 15 | 65 | 4 | 65 |
| 14 | 67 | 3 | 70 |
| 13 | 69 | 2 | 75 |
| 12 | 71 | 1 | 80 |
| 11 | 73 | 0 | 80 |
| 10 | 75 | | |
| 9 | 77 | | |
| 8 | 79 | | |
| 7 | 80 | | |

FIG. 6B

| SIT UPS-MEN | FITNESS AGE | SIT UPS-WOMEN | FITNESS AGE |
|---|---|---|---|
| 44 | 18 | 40 | 18 |
| 43 | 19 | 39 | 19 |
| 42 | 20 | 38 | 20 |
| 41 | 22 | 37 | 22 |
| 40 | 23 | 36 | 23 |
| 39 | 25 | 35 | 25 |
| 38 | 27 | 34 | 26 |
| 37 | 28 | 33 | 28 |
| 36 | 30 | 32 | 29 |
| 35 | 31 | 31 | 31 |
| 34 | 33 | 30 | 32 |
| 33 | 34 | 29 | 33 |
| 32 | 36 | 28 | 34 |
| 31 | 37 | 27 | 35 |
| 30 | 39 | 26 | 37 |
| 29 | 40 | 25 | 39 |
| 28 | 42 | 24 | 41 |
| 27 | 44 | 23 | 43 |
| 26 | 45 | 22 | 45 |
| 25 | 47 | 21 | 47 |
| 24 | 50 | 20 | 49 |
| 23 | 53 | 19 | 51 |
| 22 | 55 | 18 | 53 |
| 21 | 57 | 17 | 55 |
| 20 | 59 | 16 | 57 |
| 19 | 61 | 15 | 59 |
| 18 | 63 | 14 | 61 |
| 17 | 65 | 13 | 63 |
| 16 | 67 | 12 | 65 |
| 15 | 69 | 11 | 67 |
| 14 | 70 | 10 | 69 |
| 13 | 71 | 9 | 71 |
| 12 | 72 | 8 | 73 |
| 11 | 73 | 7 | 75 |
| 10 | 74 | 6 | 77 |
| 9 | 75 | 5 | 79 |
| 8 | 76 | 4 | 80 |
| 7 | 77 | 3 | 80 |
| 6 | 78 | 2 | 80 |
| 5 | 79 | 1 | 80 |
| 4 | 80 | 0 | 80 |
| 3 | 80 | | |
| 2 | 80 | | |
| 1 | 80 | | |
| 0 | 80 | | |

FIG. 7A

| AGE GROUP | 18-29 | | 30-39 | | 40-49 | | 50-59 | | 60-80 | |
|---|---|---|---|---|---|---|---|---|---|---|
| | MEN | WOMEN | MEN | WOMEN | MEN | WOMEN | MEN | WOMEN | MEN | WOMEN |
| VERY LEAN | <7% | <12% | <7% | <12% | <7% | <12% | <7% | <12% | <7% | <12% |
| EXCELLENT | 7% | 12% | 7% | 12% | 7% | 12% | 7% | 12% | 7% | 12% |
| GOOD | 10% | 15% | 11% | 16% | 13% | 17% | 14% | 18% | 15% | 19% |
| AVERAGE | 13% | 19% | 14% | 20% | 16% | 21% | 17% | 22% | 18% | 23% |
| FAIR | 20% | 28% | 21% | 29% | 23% | 30% | 24% | 31% | 25% | 32% |
| POOR | 23% | 31% | 24% | 32% | 26% | 33% | 27% | 34% | 28% | 35% |
| OBESE | >23% | >31% | >24% | >32% | >26% | >33% | >27% | >34% | >28% | >35% |

FIG. 7B

| MEN | FITNESS AGE | WOMEN | FITNESS AGE |
|---|---|---|---|
| <14% | 18 | <20% | 18 |
| 14.0% | 20 | 20.0% | 20 |
| 15.5% | 21 | 21.0% | 21 |
| 15.0% | 22 | 22.0% | 22 |
| 16.0% | 23 | 23.0% | 23 |
| 17.0% | 25 | 24.0% | 25 |
| 17.1% | 26 | 24.1% | 26 |
| 17.2% | 27 | 24.2% | 27 |
| 17.3% | 28 | 24.3% | 28 |
| 17.4% | 29 | 24.4% | 29 |
| 17.5% | 30 | 24.5% | 30 |
| 17.6% | 31 | 24.6% | 31 |
| 17.7% | 32 | 24.7% | 32 |
| 17.8% | 33 | 24.8% | 33 |
| 17.9% | 34 | 24.9% | 34 |
| 18.0% | 35 | 25.0% | 35 |
| 18.2% | 36 | 25.1% | 36 |
| 18.4% | 37 | 25.2% | 37 |
| 18.6% | 38 | 25.3% | 38 |
| 18.8% | 39 | 25.4% | 39 |
| 19.0% | 40 | 25.5% | 40 |
| 19.2% | 41 | 25.6% | 41 |
| 19.4% | 42 | 25.7% | 42 |
| 19.6% | 43 | 25.8% | 43 |
| 19.8% | 44 | 25.9% | 44 |
| 20.0% | 45 | 26.0% | 45 |
| 20.1% | 46 | 26.1% | 46 |
| 20.2% | 47 | 26.2% | 47 |
| 20.3% | 48 | 26.3% | 48 |
| 20.4% | 49 | 26.4% | 49 |
| 20.5% | 50 | 26.5% | 50 |
| 20.6% | 51 | 26.6% | 51 |
| 20.7% | 52 | 26.7% | 52 |
| 20.8% | 53 | 26.8% | 53 |
| 20.9% | 54 | 26.9% | 54 |
| 21.0% | 55 | 27.0% | 55 |
| 21.1% | 56 | 27.1% | 56 |
| 21.2% | 57 | 27.2% | 57 |
| 21.3% | 58 | 27.3% | 58 |
| 21.4% | 59 | 27.4% | 59 |
| 21.5% | 60 | 27.5% | 60 |
| 21.6% | 61 | 27.6% | 61 |
| 21.7% | 62 | 27.7% | 62 |
| 21.8% | 63 | 27.8% | 63 |
| 21.9% | 64 | 27.9% | 64 |
| 22.0% | 65 | 28.0% | 65 |
| 22.2% | 66 | 28.3% | 66 |
| 22.4% | 67 | 28.5% | 67 |
| 22.6% | 68 | 28.8% | 68 |
| 22.8% | 69 | 29.0% | 69 |
| 23.0% | 70 | 29.3% | 70 |
| 23.2% | 71 | 29.5% | 71 |
| 23.4% | 72 | 29.8% | 72 |
| 23.6% | 73 | 30.0% | 73 |
| 23.8% | 74 | 30.3% | 74 |
| 24.0% | 75 | 30.5% | 75 |
| 24.2% | 76 | 30.8% | 76 |
| 24.4% | 77 | 31.0% | 77 |
| 24.6% | 78 | 31.3% | 78 |
| 24.8% | 79 | 31.6% | 79 |
| 25.0% | 80 | 32.0% | 80 |

ARTICLE, SYSTEM AND METHOD FOR DETERMINING A FITNESS AGE FOR AN INDIVIDUAL

FIELD OF THE INVENTION

The present invention relates to articles, systems and methods for assessing the physical fitness condition of an individual.

BACKGROUND OF THE INVENTION

The public is becoming ever increasingly aware of their individual physical fitness. Often, from a medical standpoint, an individual's state of fitness may be assessed by blood pressure, cholesterol levels, at rest heart rate and the like. These measurements, when compared to a suggested standard or range relative to that person's age and sex, can indicate a person's physical fitness and suggest certain lifestyle changes to increase the state of their fitness. Typically, except for heart rate, the values of cholesterol and such are not indexed for age.

It would be useful if a system and method were developed which could measure certain physical parameters and, from those measurements, determine an individual's effective, fitness age. That is, if a person is sixty years old, the parameters measured may enable an assessment to be made that the person has an effective age, or fitness age, of 45. Thus, because of the measurement of these parameters, this hypothetical individual is "younger" than his chronological age. This information would be useful to an individual to provide guidelines to measure the improvements and declines in the person's overall physical fitness period. This information would also be useful from an insurance assessment standpoint to determine the individual's risk and therefore the premiums to be charged. Corporate organizations could use the information to provide guidelines for a corporate wellness program.

Accordingly, it is an object of the present invention to provide an article, system and method to assess the physical condition of an individual. It is also an object of the present invention to provide, based upon the measurement of certain physical parameters, a system, method and article to determine the individual's overall fitness age which may be the same as, less than, or greater than their chronological age.

SUMMARY OF THE INVENTION

There is, therefore, set forth according to the present invention an article, system and method directed to the above-noted objects. The article comprises a computer usable medium having computer readable program code means embodied therein for enabling the user to determine an overall fitness age by inputting into the computer parameters of at least a plurality of a heart recovery rate, flexibility, strength and body fat composition. The computer readable program means causes the computer to store at least a plurality of, in a first data structure, data correlating a physically measured heart recovery rate to an assigned heart recovery fitness age, in a second data structure, data correlating a physically measured flexibility to an assigned flexibility fitness age, in a third data structure, data correlating physically measured strength to an assigned strength fitness age and in a fourth data structure, data correlating physically measured body fat composition to a body composition fitness age. The computer readable program means correlates from each input parameter the corresponding fitness age, i.e., heart recovery fitness age, flexibility fitness age, strength fitness age and body composition fitness age and from those separate fitness ages calculates an overall fitness age for the individual. Computer code means display at the computer display the determined overall fitness age.

In a preferred embodiment, each of the above-identified parameters of heart recovery fitness age, flexibility fitness age, strength fitness age and body composition fitness age are determined in the overall fitness as calculated according to the following formula:

Overall fitness age=(0.30) heart recovery fitness age+(0.21) flexibility fitness age+(0.21) strength fitness age+(0.28) body composition fitness age.

The system includes a data processor including at least a plurality of data structures containing data correlating physically measured heart recovery rates, flexibility, strength and body fat to fitness ages, means for inputting the physical data into the data processor, the processor from the inputted data accessing the data structures to determine the separate fitness ages and the overall fitness age for the individual. Means are provided for displaying the determined overall fitness age.

The method according to the present invention includes providing a data processor including the above-described data structures, inputting data into the processor data corresponding to the physically measured parameters of heart recovery rate, flexibility, strength and body fat composition whereupon the processor determines the overall fitness age and displaying the determined overall fitness age.

According to the present invention, an individual can assess their fitness age (which might be different from their chronological age) based upon measured, physical parameters which they themselves can measure. Accordingly an individual can determine their fitness age and alter their diet, physical exercise, and flexibility to better their determined fitness age and overall well being.

BRIEF DESCRIPTION OF THE DRAWINGS

These, and other features and advantages, will be better appreciated as the same becomes better understood with reference to the specification, claims and drawings wherein:

FIG. 2 is a logic diagram illustrating the program code means, system and method according to the present invention;

FIG. 3A is a tabulation of the correlation between heart recovery rate and assigned heart recovery fitness ages;

FIG. 4A is a correlation between flexibility, age groups for men and women and ratings from excellent to poor;

FIG. 4B is a tabulation of the correlation between flexibility and assigned fitness ages;

FIG. 5A is a correlation between strength as represented by numbers of push-ups, age groups for men and women and ratings from excellent to poor;

FIG. 5B is a tabulation of the correlation between the number of push-ups and assigned fitness ages;

FIG. 6A is a correlation between strength as represented by numbers of sit-ups, age groups for men and women and ratings from excellent to poor;

FIG. 6B is a tabulation of the correlation between the number of sit-ups and assigned fitness ages;

FIG. 7A is a correlation between body fat percentages, age groups for men and women and ratings from excellent to poor; and FIG. 7B is a tabulation of the correlation between body fat and assigned fitness ages.

DESCRIPTION

Figure 1:
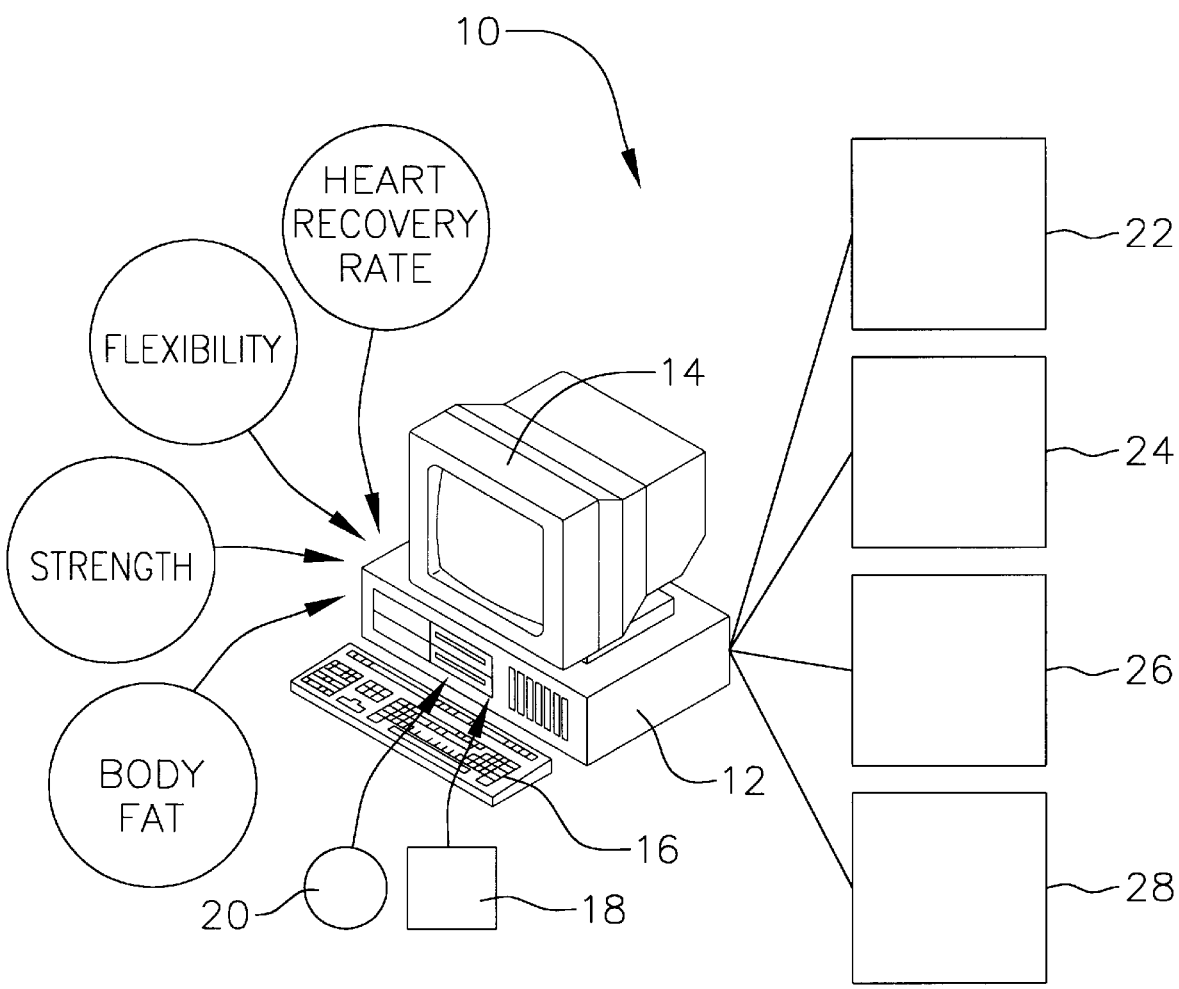
FIG. 1 illustrates the system and the input of data.

Turning to FIG. 1, a system 10 according to the present invention is provided which includes a processor 12 which may be a standard personal computer. Associated with the processor 12 is a video display 14 as well as data input means such as a keyboard 16, mouse, or the like. While not shown, a printer may also be provided for issuing a hard copy of the results or individual fitness assessment during operation of the system.

Figure 3B:
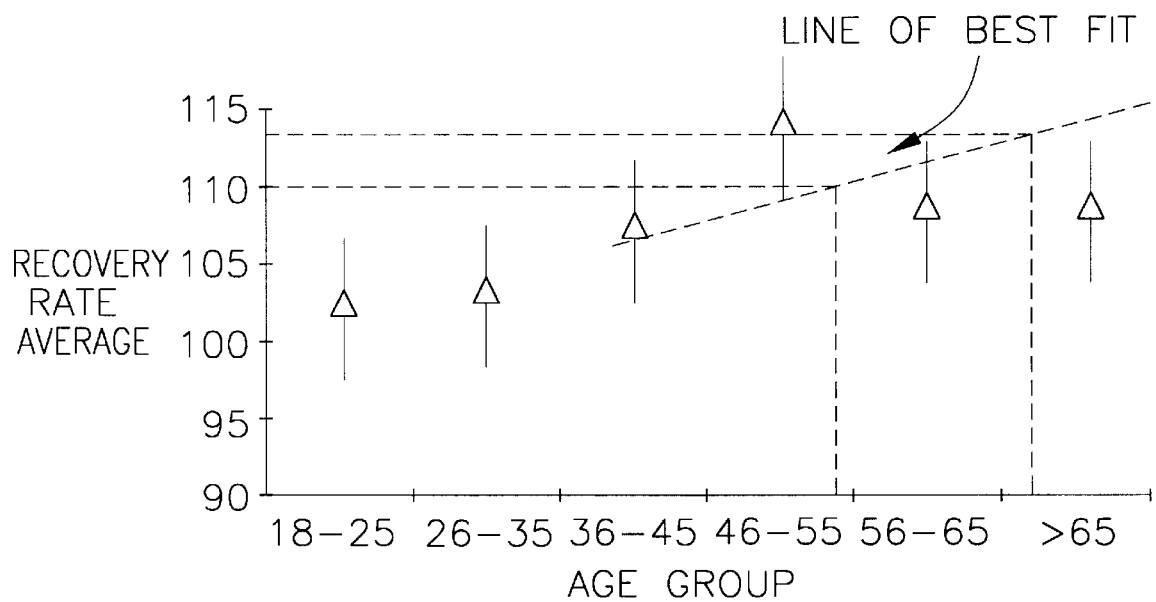
FIG. 3B is a graph showing heart recovery rate versus age groups for men and a best fit line.
Figure 3C:
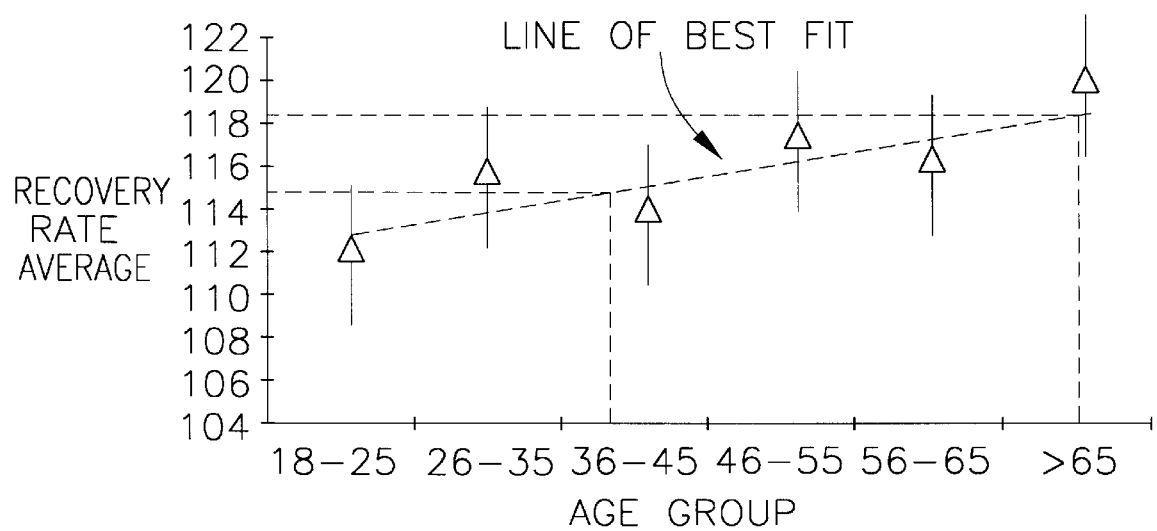
FIG. 3C is a graph showing heart recovery rate versus age groups for women and a best fit line.

The processor 12 is programmed by an article of manufacture comprising a computer usable medium having a computer readable program code means such a 3½ inch floppy disk 18 and/or compact disk 20. As programmed the processor 12 includes a first data structure 22 containing data which correlates an individual's heart recovery rate data to an assigned heart recovery fitness age. This data stored in the first data structure 22 may be as suggested in the tabulation of FIG. 3A which is derived from a graphic representation showing a correlation between recovery heart rates and average recovery heart rates for certain age groups for men and women as shown in FIGS. 3B and 3C. By taking the average recovery rates for those age groups and locating a best fit line through them, a correlation can be obtained resulting in the tabulation of FIG. 3A. The average recovery rate data shown in the graphical representations in FIGS. 3B and 3C was obtained from *American College of Sports Medicine: Research Manual for Guidelines for Exercise Testing and Prescription, 2$^{nd}$ Edition*, 1993. However, to obtain individual fitness ages as shown in the tabulation of FIG. 3A, a best fit line was required as well as certain extrapolations to derive the tabulation of FIG. 3A. Accordingly the tabulation of FIG. 3A represents an assessment, based upon the data of FIGS. 3B and 3C and the best fit line shown thereon, of the correlation between heart recovery rates and what I assigned as fitness ages.

The heart recovery rate relates to the pulse rate per minute after a vigorous step test. The individual goes up and down a set of steps for approximately 3 minutes which elevates the heart (pulse) rate. The individual discontinues the stepping and after one minute of rest measures the pulse rate in beats per minute. When the pulse rate has been obtained, through the data input means such as the keyboard 16, the individual inputs his or her measured pulse rate into the processor 12. For example, if the individual had a measured pulse rate of 104, that data would be entered into the processor 12 which would retrieve, from the first data structure 22, if the individual was a man, a corresponding heart recovery fitness age of 32. That retrieved heart recovery fitness age would be stored in memory and, if desired by the individual, displayed at the display 14. Thus if the individual had a chronological age of 50, they would be pleased that their cardio/vascular age, corresponding to their heart recovery fitness age, is much younger.

The processor 12 is also programmed through disk 18 or compact disk 20 to have a second data structure 24 correlating flexibility to an assigned flexibility age. With reference to FIGS. 4A, 4B, for certain age groups various assessments of flexibility based upon the individual's ability to reach (with legs straightened) their toes. For example, in the age group of 18–29, a man who can extend his fingertips six inches past his toes with legs straightened is deemed to have excellent flexibility. The ratings for the age groups shown in FIG. 4A are taken from the *American College of Sports Medicine: Research Manual for Guidelines for Exercise Testing and Prescription, 2$^{nd}$ Edition*, 1993, Table 19-10, page 244. Based upon the rating table of FIG. 4A, a tabulation was derived which is shown in FIG. 4B. Again, the tabulation of FIG. 4B is based upon an approximately best line fit through the flexibility ranges for each age group and assigning fitness ages to a certain flexibility measurement. The data of FIG. 4B is stored in the second data structure 24.

To obtain a flexibility fitness age, the individual reaches towards his or her toes and determines the distance the fingertips extend past or fall short of the toes with the feet straight up. This measurement, in inches, is input by the keyboard 16 into the processor 12. The processor 12, as programmed, accesses the second data structure 24 and based upon the input data retrieves a corresponding fitness age. For example, if a man can extend his fingertips four inches past his toes, the processor 12 would retrieve from the second data structure 24 a corresponding flexibility fitness age of 19. If desired, this flexibility fitness age of 19 can be displayed at the display 14. It is to be understood that additional flexibility measurements such as at the shoulder and the like could be factored as well into drawing a correlation between flexibility and assigned fitness ages.

The processor 12 is also programmed to have a third data structure 26 which correlates parameters of strength to a strength fitness age. With reference to FIG. 5A, a table is shown rating strength based upon the number of push ups an individual can do nonstop and based upon certain age groups. Again this data is obtained from the *American College of Sports Medicine: Research Manual for Guidelines for Exercise Testing and Prescription, 2$^{nd}$ Edition*, 1993, Table 19-19, page 243. As with the other data structures, a graph was generated showing the various ranges for the age groups and from that graph a best fit line was obtained and from that line a tabulation as shown in FIG. 5B was conceived correlating, for men and women, a fitness age based upon the number of push ups the individual is able to do nonstop. The third data structure 26 also, in the strength category, provides a correlation between the number of sit ups an individual can do nonstop and a fitness age. With reference to FIG. 6A, a table is shown for men and women in age groups based upon the number of sit ups they can do nonstop. This data is obtained from the *American College of Sports Medicine: Research Manual for Guidelines for Exercise Testing and Prescription. 2$^{nd}$ Edition*, 1993, Table 19-19, page 243. From that table, a graph was created and from that graph and a best line fit, the tabulation shown in FIG. 6B was conceived. For example, if a man is able to do 40 sit ups nonstop, that would correspond to an assigned sit up strength fitness age of 23.

Accordingly, an individual does as many push ups as they can do nonstop as well as sit ups and inputs that data by the keyboard 16 into the processor 12. The processor 12 looks up the corresponding tables (FIGS. 5B and 6B) in the third data structure 26 and from that retrieves corresponding strength fitness ages for push ups and sit ups and stores the retrieved fitness ages in memory. The retrieved fitness ages can also be displayed at the display 14.

The processor 12 is also programmed to have a fourth data structure which correlates body fat composition to a corresponding body fat fitness age. FIG. 7A shows a tabulation for various age groups for men and women for body fat percentages to certain ratings from very lean to obese. This table shown in FIG. 7A was obtained from the American College of Sports Medicine. The percentages are calculated from the following formulas:

For men: [(0.567×waist)+(0.101×age)−31.8]+[(−98.42+4.15× waist−0.082×weight)÷weight]÷2.

For women: [(1.21×BMI)+(0.262×age)−6.7]+[(−76.76+4.15×waist− 0.082×weight)÷weight]÷2.

Where BMI is body mass index represented by the formula:

BMI=weight÷height$^2$ (using variables measured in metric units only).

It is to be understood that body fat can also be measured by buoyancy or modernly by devices which rely upon electrical potential. Suffice it to say, that by any suitable means, a body fat percentage can be obtained.

From the table of FIG. 7A, a tabulation was derived as shown in FIG. 7B correlating body fat percentage to a corresponding body fat fitness age. Thus an individual having a twenty percent body fat would have a corresponding body fat fitness age of 45.

The individual after obtaining his or her body fat percentage, inputs that data by the keyboard 16 into the processor 12. The processor 12 accesses the fourth data structure 28 and from that retrieves the corresponding body fat fitness age which is stored in memory. If desired, the corresponding body fat fitness age can also be displayed at the display 14. For that matter, all of the determined fitness ages can be simultaneously displayed at display 14.

After the individual has obtained and input the various parameters and obtained the heart recovery fitness age, flexibility fitness age, strength fitness age, and body fat fitness age, an overall fitness age can now be determined for the individual. For that purpose, I have weighted the various determined fitness ages in the following manner. I weighted heart recovery fitness age at a thirty percent (30%) weighting, flexibility at a twenty-one percent (21%) weighting, a strength fitness age weighting of twenty-one percent (21%), half of that (10.5%) from the push up fitness age and the other half (10.5%) from the sit up fitness age, and body fat fitness age at twenty-eight percent (28%). Accordingly, the overall fitness age of the individual can be determined by the following equation:

$$\text{Overall fitness age} = .30 \times \text{heart recovery fitness age} +$$
$$.21 \times \text{flexibility fitness age} +$$
$$.21 \times \text{strength fitness age} +$$
$$.28 \times \text{body fat fitness age}.$$

The processor 12, from the stored individual fitness ages, calculates the overall fitness age and issues signals to display the same at the display 14.

With reference to FIG. 2, the operation of the system and method according to the present invention is shown. At 30 the program is installed in the processor 12 by inserting the floppy disk 18 or CD-ROM disk 20 into the suitable port of the processor 12. After the loading the program, the processor sends signals to the display 14 providing instructions on how to determine one's overall fitness age.

At 34, the individual inputs their heart recovery rate in beats per minute by the keyboard 16 into the processor 12 which at 36 compares the input data to the data stored in the first data structure 22 to find the heart recovery fitness age which is stored at 40 in a suitable cache memory. At 42 the individual inputs their flexibility in inches, determined in the manner described above, whereupon the processor at 44 searches the second data structure 24 to locate the corresponding flexibility fitness age which in turn is stored at 46 in a cache memory. At 48 the individual inputs their strength parameters as measured in the manner described above and the processor at 50 searches the third data structure 26 to obtain the strength fitness age from the individual push up and sit up fitness ages which is stored at 52 in cache memory. At 54 the individual inputs their body fat percentage whereupon the processor at 56 accesses the fourth data structure 28 to find the corresponding fitness age which is stored at 58 in cache memory. At 60, the processor 12 from the fitness ages stored in the cache memory, calculates the overall fitness age according to the equation identified above and at 62 displays the same at the display 14.

Using the displayed overall fitness age, the individual can gauge their overall status of physical fitness by comparing their fitness age to their chronological age. For example, an individual 60 years old may have a fitness age of 45 indicating that they are relatively fit. An individual having a fitness age greater than their chronological age, may be prompted to increase their strength, cardiovascular fitness, flexibility and reduce their body fat to better their fitness age.

Furthermore, by determining fitness ages over time, an individual can assess their progress. Over time, if the fitness age is dropping or staying the same, that indicates that the individual is bettering their overall fitness, in comparison to other individuals of that age.

While I have shown and described certain embodiments of the present invention, it is to be understood that it is subject to many modifications and changes without departing from the spirit and scope of the claims. For example, other parameters may be used to calculate fitness age such as at rest, pulse rate, and even clinical parameters such as blood pressure and cholesterol could be integrated into the calculation of the overall fitness age. Furthermore, one does not need each of the parameters of heart recovery rate, flexibility, strength and body fat and may instead select only a plurality of these factors to determine a fitness age.

I claim:

1. An article of manufacture comprising a computer usable medium having computer readable program code means embodied therein for enabling the user to determine an overall fitness age by inputting into the computer parameters of at least a plurality of (i) heart recovery rate, (ii) flexibility, (iii) strength and/or (iv) body fat composition, said determined overall fitness age displayed at a display, the program code means in said article of manufacture comprising:

computer readable program code means for causing the computer to store at least a plurality of,
(i) in a first data structure data correlating a heart recovery rate to an assigned heart recovery fitness age,
(ii) in a second data structure data correlating flexibility to an assigned flexibility age,
(iii) in a third data structure data correlating strength to an assigned strength age,
(iv) in a fourth data structure data correlating body fat composition to a body composition age,
computer readable program code means for correlating from each input parameter the corresponding fitness age and therefrom for determining an overall fitness age; and
computer code means for displaying at the display the determined overall fitness age.

2. The article of manufacture of claim 1 wherein said computer readable program means for determining the overall fitness age assigns an unequal weighting to a plurality of said corresponding fitness ages.

3. The article of manufacture of claim 2 wherein said computer program means determines the overall fitness age according to the following equation:

Overall Fitness Age=(0.30) heart recovery fitness age+(0.21) flexibility age+(0.21) strength age+(0.28) body composition age.

4. A system for determining an overall fitness age for an individual as determined by at least a selected plurality of fitness parameters of (i) heart recovery rate, (ii) flexibility, (iii) strength and (iv) body composition comprising:

a data processor including at least a plurality of,
(i) a first data structure containing data correlating heart recovery rate to an assigned heart recovery fitness age,
(ii) a second data structure containing data correlating flexibility to an assigned flexibility fitness age,
(iii) a third data structure containing data correlating strength to an assigned strength fitness age, and
(iv) a fourth data structure containing data correlating body fat composition to an assigned body composition fitness age, data input means for inputting data into the processor data corresponding to physically measured parameters of the individual of heart recovery rate, flexibility, strength and body fat composition, said processor from said inputted
data determining an overall corresponding fitness age for the individual; and
means for displaying the determined overall fitness age.

5. The system of claim 4 wherein said processor is adapted to determine the overall fitness age according to the following equation, Overall Fitness Age=(0.30) heart recovery fitness age+(0.21) flexibility fitness age+(0.21) strength fitness age+(0.28) body composition fitness age.

6. A method for determining an overall fitness age for an individual as determined by at least a selected plurality of fitness parameters of (i) heart recovery rate, (ii) flexibility, (iii) strength and (iv) body composition comprising:

providing a data processor including at least a plurality of,
(i) a first data structure containing data correlating heart recovery rate to an assigned heart recovery fitness age,
(ii) a second data structure containing data correlating flexibility to an assigned flexibility fitness age,
(iii) a third data structure containing data correlating strength to an assigned strength fitness age, and
(iv) a fourth data structure containing data correlating body fat composition to an assigned body composition fitness age,
inputting data into the processor data corresponding to physically measured parameters of the individual of heart recovery rate, flexibility, strength and body fat composition, said processor from said inputted data determining an overall corresponding fitness age for the individual; and
displaying the determined overall fitness age.

7. The method of claim 6 determining the overall fitness age according to the following equation, Overall Fitness Age=(0.30) heart recovery fitness age+(0.21) flexibility fitness age+(0.21) strength fitness age+(0.28) body composition fitness age.

* * * * *